(12) United States Patent
Newton (10) Patent No.: US 8,707,965 B2
(45) Date of Patent: *Apr. 29, 2014

(54) ELECTRONIC CIGARETTE WITH LIQUID RESERVOIR

(71) Applicant: Kyle D. Newton, Colleyville, TX (US)

(72) Inventor: Kyle D. Newton, Colleyville, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/955,153

(22) Filed: Jul. 31, 2013

(65) Prior Publication Data

US 2013/0312776 A1  Nov. 28, 2013

Related U.S. Application Data

(63) Continuation of application No. 13/157,024, filed on Jun. 28, 2011, now Pat. No. 8,528,569.

(51) Int. Cl.
*A24F 47/00* (2006.01)
(52) U.S. Cl.
USPC .................. 131/273; 131/194; 128/202.21
(58) Field of Classification Search
None
See application file for complete search history.

(56) References Cited

U.S. PATENT DOCUMENTS

| 8,528,569 | B1 * | 9/2013 | Newton | 131/194 |
| 2005/0172976 | A1 * | 8/2005 | Newman et al. | 131/194 |
| 2012/0111347 | A1 * | 5/2012 | Hon | 131/329 |

FOREIGN PATENT DOCUMENTS

CN          201379072 Y  *  1/2010

* cited by examiner

*Primary Examiner* — Richard Crispino
*Assistant Examiner* — Eric Yaary
(74) *Attorney, Agent, or Firm* — Daniel R. Brown; Dan Brown Law Office (57) ABSTRACT

An electronic cigarette including an elongated housing that has a mouthpiece with an aerosol outlet, and an atomizer disposed within an atomizing chamber. The atomizer selectively generates an aerosol of the liquid in response to suction pressure at the aerosol outlet. The atomizing chamber has an air inlet, an atomizer outlet coupled to the aerosol outlet, and a first wick aperture. A liquid reservoir is disposed within the elongated housing, which is sealably separated from the atomizing chamber. A wick disposed through the first wick aperture between the liquid reservoir and the atomizing chamber and it is configured to transfer the liquid by capillarity from the liquid reservoir to the atomizer.

15 Claims, 7 Drawing Sheets

ELECTRONIC CIGARETTE WITH LIQUID RESERVOIR

BACKGROUND OF THE INVENTION

1. Field of the Invention

The present invention relates to electronic cigarettes. More specifically, the present invention relates to an electronic cigarette with an internal liquid reservoir.

2. Description of the Related Art

Electronic cigarettes have become increasingly popular in recent times. Electronic cigarettes emulate a tobacco cigarettes, but without the combustion of tobacco during use. Rather than burning tobacco, a liquid is atomized within the electronic cigarette, which emulates the smoke produced in a tobacco cigarette. The liquid may contain flavoring agents such as tobacco flavor, menthol, and others, to enhance the "smoking" experience of the electronic cigarette. Nicotine has been added to the atomization liquid in prior art electronic cigarettes. In certain prior art electronic cigarettes, a reserve of liquid is stored within the cigarette housing in a porous material, which is placed into contact with an atomizing assembly such that the liquid can be gradually transferred to the atomizing assembly during consumption. A replaceable cartridge with a liquid soaked porous material has been provided to enable consumers to replenish the supply of liquid as it is depleted during use by replacing the cartridge. It should be appreciated that the structural and electrical components in an electronic cigarette are durable and outlast, by a long measure, the period of consumption for the quantity of liquid provided in such a porous reservoir.

Consumers of electronic cigarettes are experienced at replacing the liquid reservoir cartridges as the liquid is depleted during consumption. In fact, it is common for consumers to carry spare cartridges so that they are readily available in the event their current cartridge becomes depleted. In fact, this arrangement can become somewhat tedious after a period of use, and there is a general desire on the marketplace to extend the duration of use between cartridge changes, or even the elimination of the need to ever change cartridges. Thus is can be appreciated that there is a need in the art for an apparatus for increasing the quantity of liquid stored within an electronic cigarette and other means to reduce the frequency of replacing or adding additional liquid during use.

SUMMARY OF THE INVENTION

The need in the art is addressed by the apparatus of the present invention. The present invention teaches an electronic cigarette apparatus including an elongated housing that has a mouthpiece with an aerosol outlet, and an atomizer disposed within an atomizing chamber. The atomizer selectively generates an aerosol of the liquid in response to suction pressure at the aerosol outlet. The atomizing chamber has an air inlet, an atomizer outlet coupled to the aerosol outlet, and a first wick aperture. A liquid reservoir is disposed within the elongated housing, which is sealably separated from the atomizing chamber. A wick disposed through the first wick aperture between the liquid reservoir and the atomizing chamber and it is configured to transfer the liquid by capillarity from the liquid reservoir to the atomizer.

In a specific embodiment, the foregoing apparatus further includes an inlet vent formed on the exterior of the elongated housing that is coupled to deliver air to the atomizing chamber air inlet. In a refinement to this embodiment, the inlet vent is coupled to the atomizing chamber air inlet by a conduit. In a further refinement, the conduit sealably passes through the liquid reservoir.

In a specific embodiment of the foregoing apparatus, the atomizer outlet and the aerosol outlet are coupled together by a chimney. In a refinement to this embodiment, the chimney sealably passes through the liquid reservoir.

In a specific embodiment of the foregoing apparatus, the atomizer is a resistive heating element. In a refinement to this embodiment, the wick is partially engages the resistive heating element.

In a specific embodiment of the foregoing apparatus, the atomizer has a tubular form defining an open central passage. In a refinement to this embodiment, the wick passes through the open central passage.

In a specific embodiment of the foregoing apparatus, the atomizing chamber further includes a second wick aperture, and the apparatus is arranged such that a first end of the wick passes through the first wick aperture and a second end of the wick passes through the second wick aperture.

In a specific embodiment of the foregoing apparatus, the wick is fabricated as a bundle of heat resistant fibers. In a refinement to this embodiment, the bundle of heat resistant fibers is fiberglass. In another refinement to this embodiment, the bundle of heat resistant fibers is fabricated from a material selected from; aramid, fluorocarbon, sulfide, melamine, polyimide, carbon, and glass.

In a specific embodiment of the foregoing apparatus, the liquid reservoir is formed as an annular cavity between the interior of the elongated housing and the atomizing chamber. In another specific embodiment of the foregoing apparatus, the liquid reservoir includes an external access opening, for enabling addition of liquid into the liquid reservoir. In a refinement to this embodiment, the external access opening is a removable mouthpiece.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope hereof and additional fields in which the present invention would be of significant utility.

In considering the detailed embodiments of the present invention, it will be observed that the present invention resides primarily in combinations of steps to accomplish various methods or components to form various apparatus and systems. Accordingly, the apparatus and system components and method steps have been represented where appropriate by conventional symbols in the drawings, showing only those specific details that are pertinent to understanding the present invention so as not to obscure the disclosure with details that will be readily apparent to those of ordinary skill in the art having the benefit of the disclosures contained herein.

In this disclosure, relational terms such as first and second, top and bottom, upper and lower, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises a" does not, without more constraints, preclude the existence of additional identical elements in the process, method, article, or apparatus that comprises the element.

The present invention advances the art of electronic cigarettes by teaching an electronic cigarette that provides a liquid reservoir, which effectively delivers liquid at the requisite rates from the reservoir to an atomizer in a open atomizing chamber. This arrangement enables production of aerosol of the liquid at desired rates of atomization without excessive liquid transfer during periods of non-use. This function is enabled though utilization of a wick aperture through the atomizing chamber and a wick disposed between the liquid reservoir and the atomizer. The wick enables the transfer of liquid by capillarity in a controlled manner without flooding the open atomization chamber.

Figure 1:
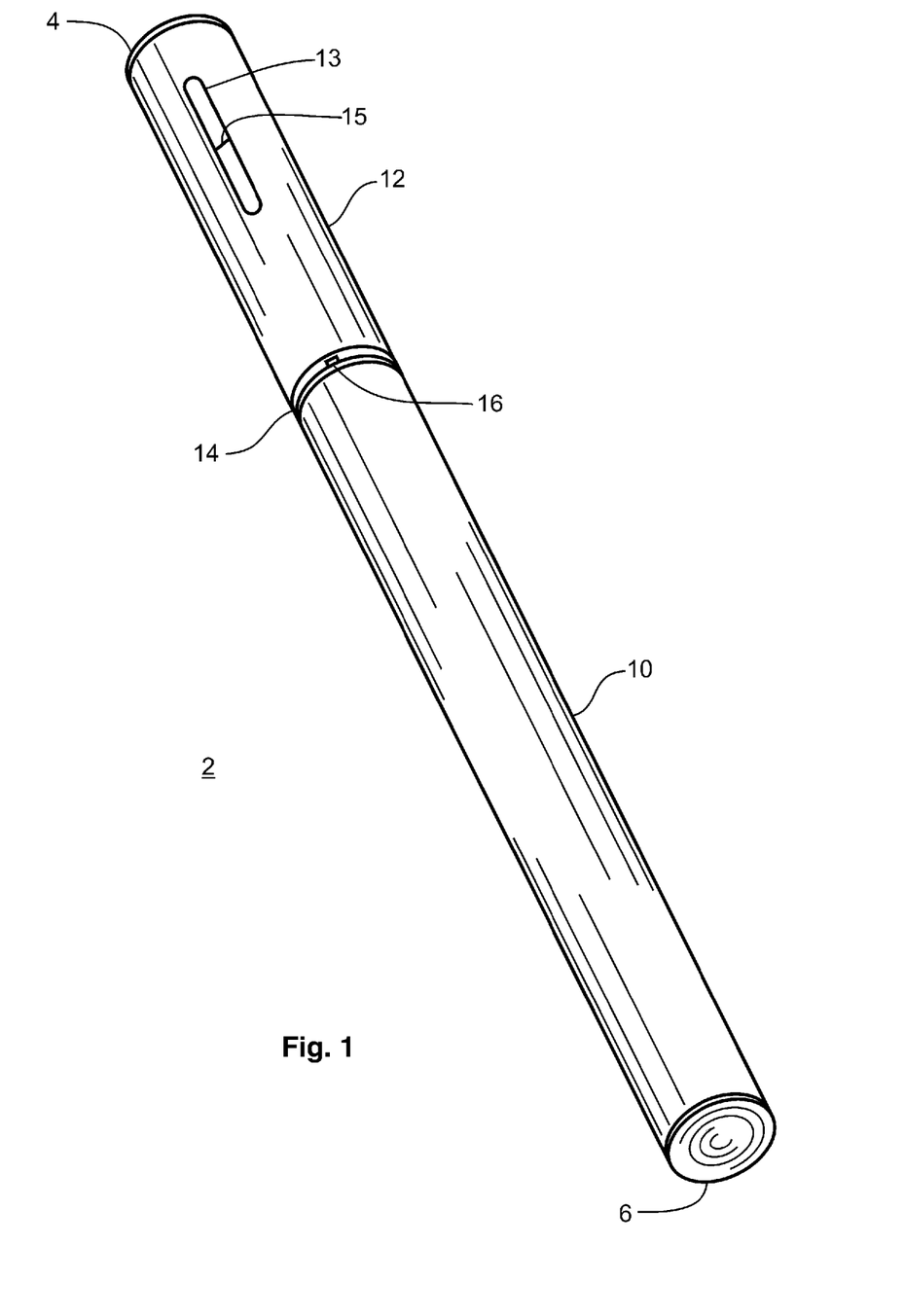
FIG. 1 is a perspective view drawing of an electronic cigarette according to an illustrative embodiment of the present invention.
Figure 2A:
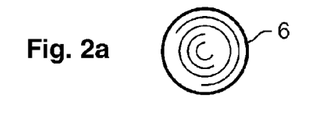
FIGS. 2a, 2b, and 2c are a tip end view, a side view, and mouthpiece end view, respectively, drawings of an electronic cigarette according to an illustrative embodiment of the present invention.
Figure 2B:
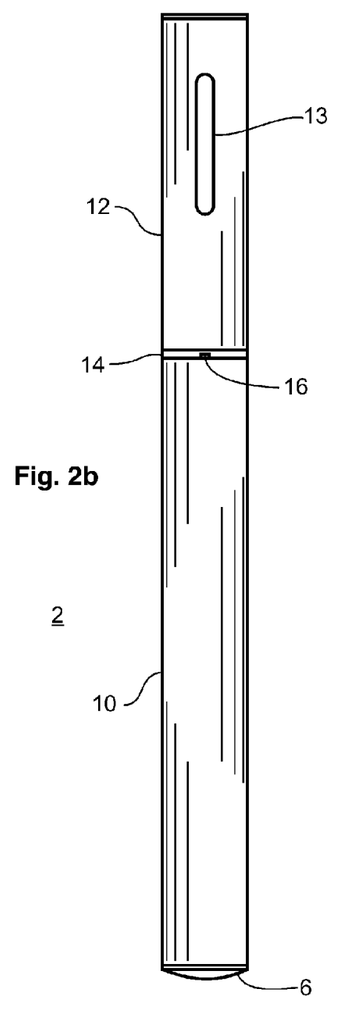
Figure 2C:
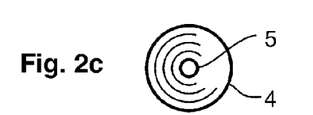
Figure 3A:
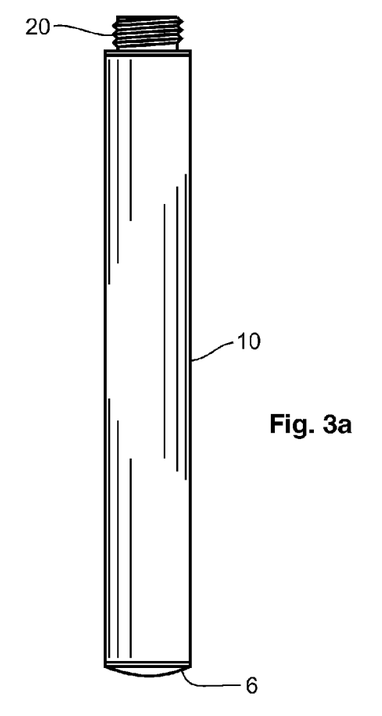
FIGS. 3a and 3b are side view drawings, respectively, of a cartridge portion and a power supply portion of an electronic cigarette according to an illustrative embodiment of the present invention.
Figure 3B:
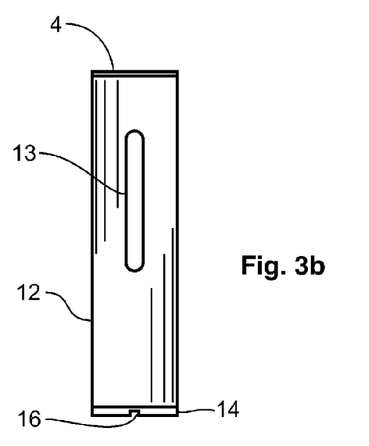
Figure 4A:
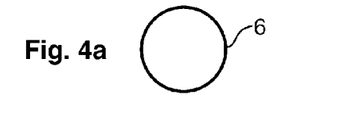
FIGS. 4a, 4b, and 4c are tip end view, side section view, and mouthpiece end view, respectively, drawings of an electronic cigarette according to an illustrative embodiment of the present invention.
Figure 4B:
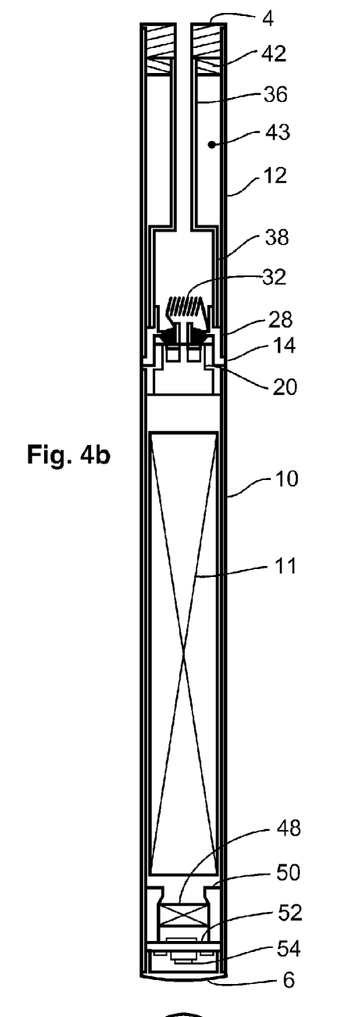
Figure 4C:
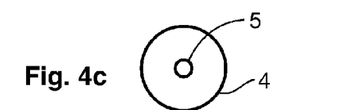
Figure 5A:
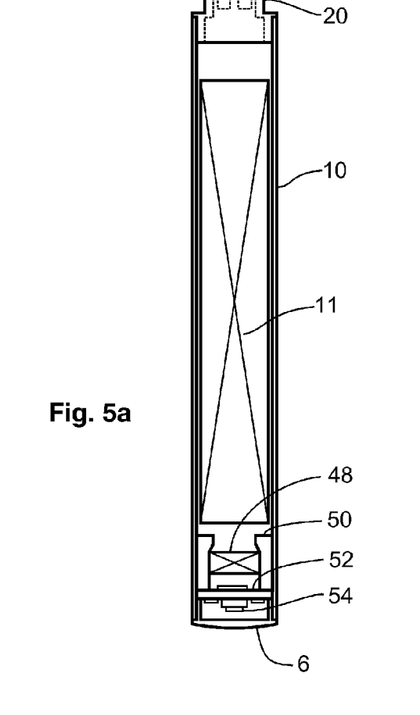
FIGS. 5a and 5b are side section view drawings, respectively, of a cartridge portion and a power supply portion of an electronic cigarette according to an illustrative embodiment of the present invention.
Figure 5B:
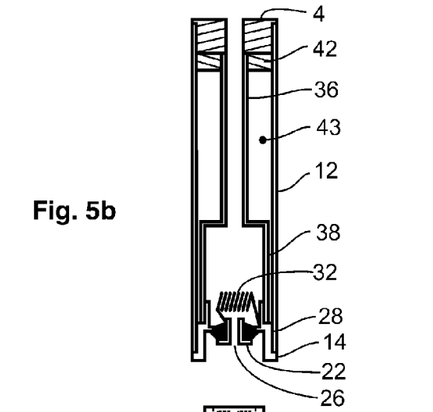

Reference is directed to FIG. 1 is a perspective view drawing of an electronic cigarette 2 according to an illustrative embodiment of the present invention. The electronic cigarette 2 comprises a housing having a first elongated portion 10 and a second elongated portion 12. The second elongated portion 12, also referred to as the "cartridge" in certain illustrative embodiments, comprises a mouthpiece end 4, which has an aerosol outlet (not shown) for drawing air through the cartridge 12. The first elongated portion 10 and the second elongated portion 12 are removable joined together with a mechanical coupler 14. One or more air inlet vents 16 are provided about the coupler 14 for allowing airflow into the cartridge 12 when the user draws air through the electronic cigarette 2. The first elongated portion 10 comprises a tip end 6, which in the illustrative embodiment, is fabricated from a translucent material enabling the transmission of light therethrough. Within the second elongated portion 12 is disposed a liquid reservoir (not fully shown). The liquid reservoir includes a clear or translucent window 13 to the exterior of the housing 12 for visually determining the liquid level 15 within the liquid reservoir.

Now, considering FIGS. 2*a*, 2*b*, and 2*c*, these are a tip end view, a side view, and mouthpiece end view, respectively, drawing of an electronic cigarette according to an illustrative embodiment of the present invention. Note that the first elongated portion 10 and second elongated portion 12 combine at coupler 14 to present a complete electronic cigarette 2 that closely resembles a tobacco cigarette. The cartridge 12 is fabricated with a finished material resembling the filter of a tobacco cigarette, and the first elongated portion 10 is fabricated to resemble the tobacco roll of a tobacco cigarette. As noted above, the cartridge 12 includes a window 13 for visually determining the liquid level of the internal liquid reservoir (not shown). The mouthpiece end 4 includes an aerosol outlet opening 5, for drawing air and aerosol out of the cartridge 12. Air is inlet to the electronic cigarette 2 at the vent openings 16 located at the coupler 14. The air inlet openings 16 can be located elsewhere on the electronic cigarette 2, and is a matter of design choice. In the illustrative embodiment, the tip end 6 is a translucent gray material resembling an ash.

Reference is directed to FIGS. 3*a* and 3*b*, which are side view drawings, respectively, of a cartridge portion 12 and a power supply portion 10 of an electronic cigarette according to an illustrative embodiment of the present invention. A threaded extension 20 on the power supply portion 10 of the housing threadably engages the mechanical coupler 14 on the cartridge portion 12. In addition, as will be described more fully hereinafter, an electrical connection is also facilitated in the connection between the threaded extension 20 and the mechanical coupler 14. The cartridge portion 12 can thusly be installed, uninstalled, and replaced as needed. The cartridge portion contains the liquid reservoir and the window 13 provides the visual cue as to the liquid remaining The tip end 4 can be removed in certain illustrative embodiments to facilitate the addition of liquid to the reservoir. The tip end 6 glow by light of an internal amber LED in response to suction pressure at the aerosol outlet 5.

Reference is directed to FIGS. 4*a*, 4*b*, and 4*c*, which are tip end view, side section view, and mouthpiece end view, respectively, drawings of an electronic cigarette according to an illustrative embodiment of the present invention. Reference is additionally directed to FIGS. 5*a* and 5*b*, which are side section view drawings, respectively, of a cartridge portion and a power supply portion of an electronic cigarette correspond to this illustrative embodiment. FIGS. 4 and 5 correspond to the same illustrative embodiment and provide details of the internal structures of the illustrative embodiment. The tip end 4 is a resilient insert that engages the interior of the cartridge housing 12 and provides the aerosol outlet 5, which is a passage formed therethrough. Within the cartridge housing 12 is an atomizing chamber 38 that has an open chimney 36 extending to the aerosol outlet 5. The chimney 36 is located within the cartridge housing by a resilient seal 42. The annular space formed between the interior of the cartridge housing 12 and the chimney 36 defines the liquid reservoir 43. At the upper end, resilient seal 42 closes and seals the liquid reservoir 43. The lower end of the reservoir 43 engages the atomizer assembly 28, which will be more fully described hereinafter.

In FIGS. 4 and 5, the atomizer assembly 28 include the atomizer 32, which is disposed within the atomizer chamber 38. In addition, the atomizer assembly 28 comprises the mechanical coupler 14 that engages the threaded extension 20 of the power supply portion 10. Within the mechanical coupler 14, and also a part of the atomizer assembly 28, is an electrical coupler 22 that has an air inlet port 26 formed therethrough, which is pneumatically coupled to the atomizing chamber 38. Thusly, the pathway for the flow of fresh air in and aerosol out includes air drawn through the mechanical coupler 14, through the air inlet port 26, to the atomizer 32 within the atomizing chamber 38, up the chimney 36 and out the aerosol outlet 5.

In FIGS. 4 and 5, the power supply portion 10 of the housing has a threaded extension 20 that engages the mechanical coupler 14. There is also a corresponding electrical connection such that the power supply portion 10 can deliver electric current to the atomizer 32 to facilitate generation of aerosol. Two conductors are provided, including the outer mechanical connection and the central pneumatic/electric connection. Suitable milling for air-flow channels is provided to facilitate solid mechanical, conductive electrical, and pneumatic connections. In the illustrative embodiment, power is derived from a storage battery 11. A pressure sensor 48 detects negative pressure within the housing 10 and energizes the atomizer. The pressure sensor 46 is located by a pressure seal 50. A draw circuit 52 provides the electrical operation functions. In addition, and amber LED 54 is disposed to illuminate through the translucent tip 6 to emulate burning ash while the draw pressure sensor 48 detects negative pressure.

Figure 6:
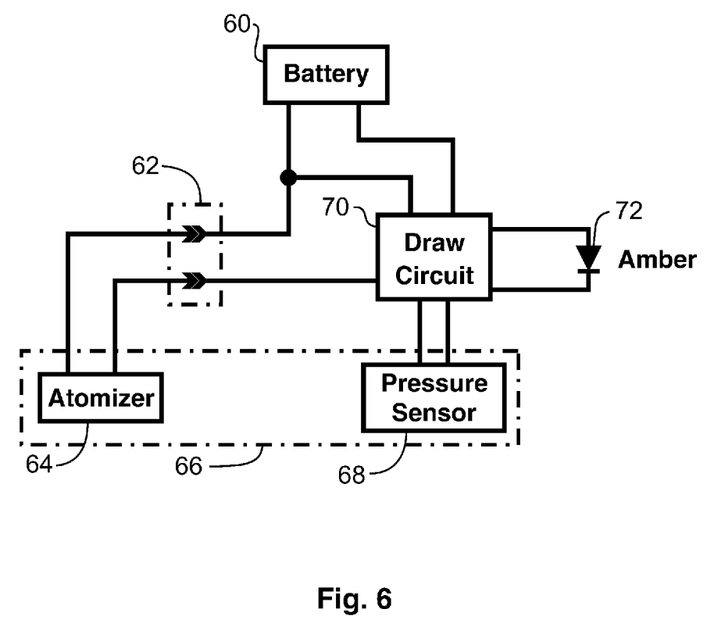
FIG. 6 is a functional block diagram an electronic cigarette according to an illustrative embodiment of the present invention.

Reference is directed to FIG. 6, which is a functional block diagram an electronic cigarette according to an illustrative embodiment of the present invention. This diagram presents the electrical functions of the electronic cigarette. The battery 60 provides power to a draw circuit 70. A pressure sensor 68 is disposed within the cigarette housing 68. When negative pressure is detected, the draw circuit 70 delivers electric power to the atomizer 64 and the amber LED 72. This action causes aerosol to be produced in the presence of the negative pressure, and the tip of the electronic cigarette to glow amber so long as the negative pressure continues. The atomizer 64 is electrically coupled to the circuit through electrical coupler 62.

Figure 7:
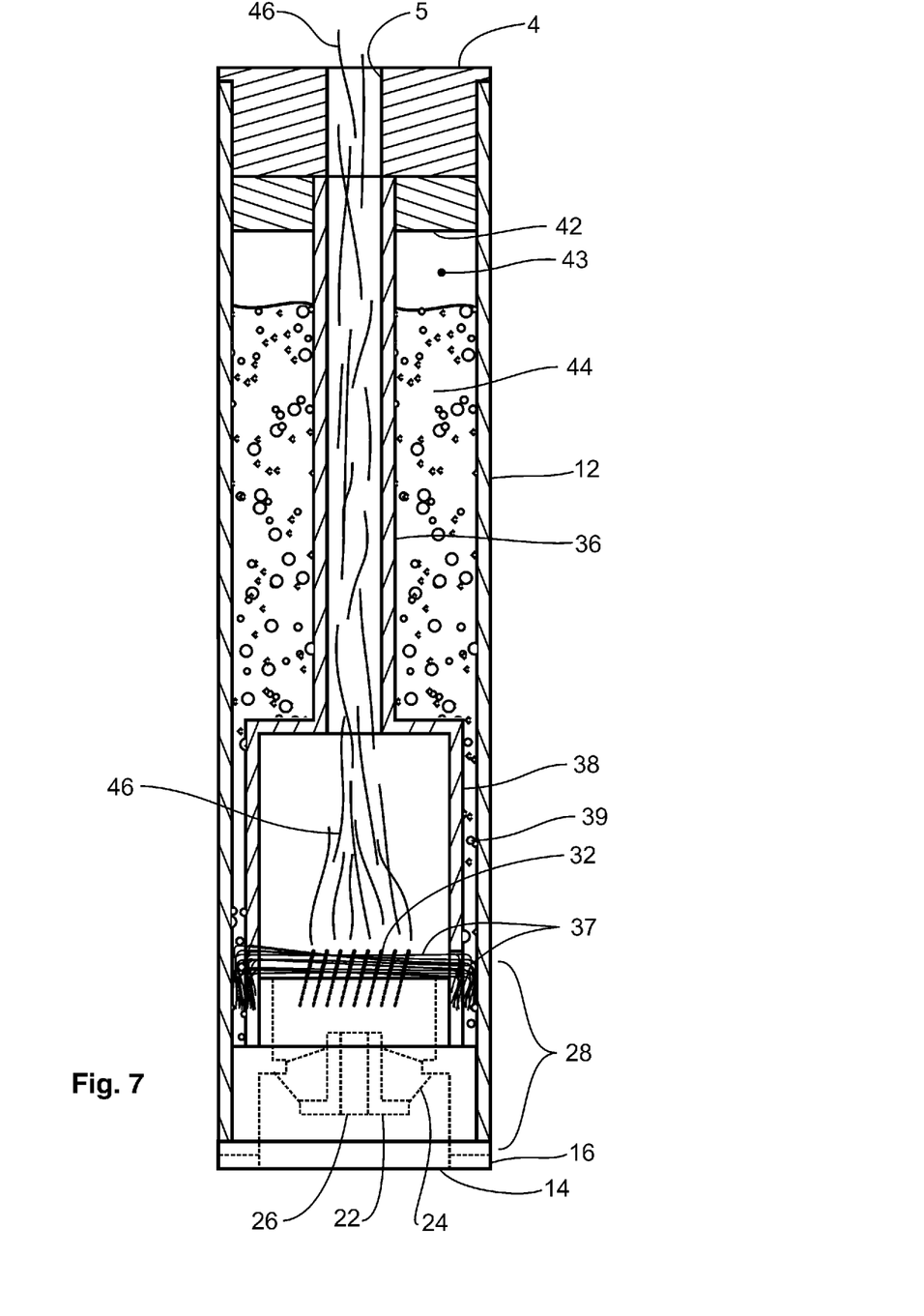
FIG. 7 is a detailed side section view drawing of a liquid reservoir cartridge according to an illustrative embodiment of the present invention.

Reference is directed to FIG. 7, which is a detailed side section view drawing of a liquid reservoir cartridge according to an illustrative embodiment of the present invention. This drawing provides further details into the structure and operation of the liquid reservoir cartridge assembly. The cartridge comprises an outer housing 12 that is closed at the upper end by the tip end resilient insert 4, which has the aerosol port 5 formed therethrough. The lower end of the housing 12 is closed with the atomizer assembly 28, which has the mechanical coupler 14 at the extreme end. Plural air inlet vents 16 are formed though the mechanical coupler so that fresh air can enter while it is secured to the power supply housing. Within the cartridge housing 12 is the atomizing chamber 38 that is pneumatically coupled to the chimney 36, which is aligned with the aerosol outlet 5. The chimney 36 is located and sealed at the upper end by resilient seal 42. The annular space 43 between the chimney 36 and the interior of the housing 12 defines the liquid reservoir 43. Note that there is a thinner annular cavity 39 formed between the exterior of the atomizing chamber 38 and interior of the cartridge housing 12. The fluid 44 is stored in the fluid reservoir 43, and is also capable of flowing into the annular cavity 39 to saturate wick 37.

In FIG. 7, the atomizing assembly 28 is comprised of several components. The atomizer 32 is a coiled nickel-chromium heater through which the wick 37 passes. The wick 37 passes through wick apertures in the atomizing chamber (not shown) on its two ends, and into the annular cavity 39. The atomizer assembly 28 is machined from a suitable metal and includes the mechanical couple 14, the electrical coupler 22, which is supported by an insulative support 24, and which has the air inlet port 26 formed therethrough. During operation, when there is a negative pressure imposed on the system by drawing air out of the aerosol outlet 5, and while electric current is delivered to the atomizer 36, air enters the air inlet port 26 and carries aerosol of the liquid 46 away from the atomizer 32, up the chimney 36 and out the aerosol outlet 5. As the liquid in the wick 37 is depleted by the atomizer 32, capillary action draws additional liquid from the liquid reservoir 43, through the cavity 39 and to the atomizer 32.

Figure 8:
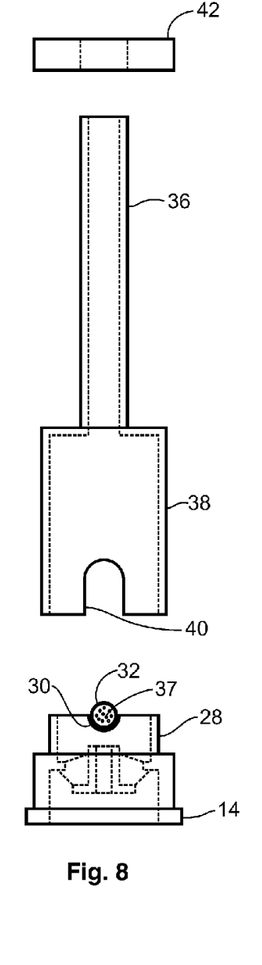
FIG. 8 is an exploded view drawing of a liquid reservoir cartridge according to an illustrative embodiment of the present invention.

Reference is directed to FIG. 8, which is an exploded view drawing of an atomizer 28, atomizing chamber 38, chimney 36 and resilient seal 42 according to an illustrative embodiment of the present invention. In the illustrative embodiment, the atomizing chamber 38 and chimney 36 are formed as a single unit. The resilient seal 42 is a donut shaped polymeric material that is pressed onto the upper end of the chimney 36. The atomizing chamber 38 includes a pair of opposing wick apertures 40 formed therein, which provide clearance for the wick 37 to pass into the atomizing chamber 38. The atomizing assembly 28 includes the mechanical coupler 14 at its lower end and the atomizer 32 at its upper end. The wick 37 passes through the center of the atomizer 32. The atomizing assembly has a pair of semicircular recesses 30 formed therein which align cooperatively with the wick apertures 40 in the atomizing chamber when the two units are engaged. This results in a circular aperture through which the wick 37 passes with a slightly compressive fit. This arrangement enables liquid to pass through by capillarity of the wick 37, but prevents the liquid from flooding the atomizing chamber 38, which would be detrimental or atomizer function.

Figure 9:
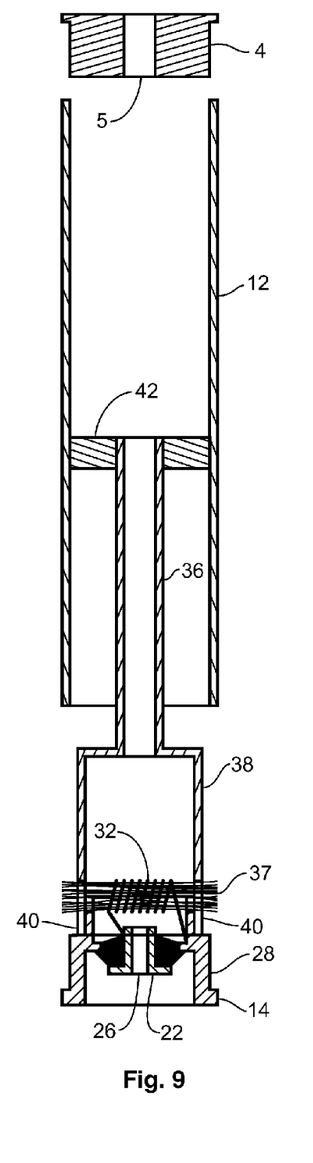
FIG. 9 is a partially exploded section view drawing of a liquid reservoir cartridge according to an illustrative embodiment of the present invention.
Figure 10:
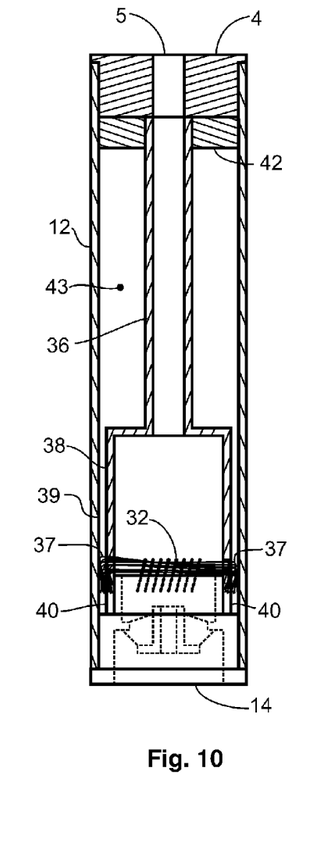
FIG. 10 is a section view drawing of a liquid reservoir cartridge according to an illustrative embodiment of the present invention.
Figure 11A:
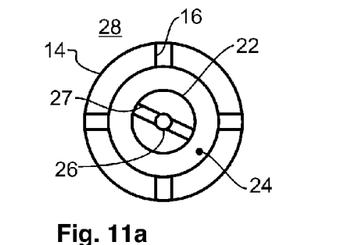
FIGS. 11a, 11b, 11c, and 11d are a first end view, a first side section view, a second end view, and a second side section view drawing, respectively, of an atomizing assembly according to an illustrative embodiment of the present invention.
Figure 11B:
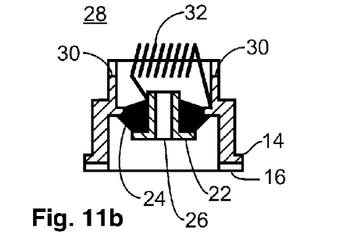
Figure 11C:
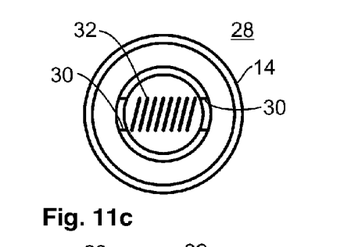
Figure 11D:
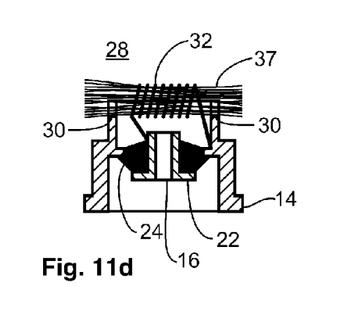

Reference is directed to FIG. 9, which is a partially exploded side section view drawing, and to FIG. 10, which is an assembled side section view drawing, of a liquid reservoir cartridge according to an illustrative embodiment of the present invention. The wick 37 passes through the atomizer 32 and extends to the outer periphery of the atomizer assembly 28. The atomizing chamber 38 is engaged with the atomizing assembly 28, thereby perfecting the wick aperture 40 as described hereinbefore, and enclosing the atomizing chamber 38. The resilient seal 42 is disposed between the exterior of the chimney 36 and the interior of the housing 12, thereby sealing the upper end of the fluid reservoir 43. The tip end resilient insert 4, with the aerosol outlet port 5, closes the upper end of the cartridge housing 12, and the chimney 36 is thereby aligned and sealed to the aerosol outlet 5. The housing 12 is engaged with the atomizer assembly 28, which urges the ends of the wick 37 downwardly and constrains them within the annular cavity 39 formed between the interior of the housing 12 and the exterior of the atomizing chamber 38. The wick 37 is thusly enabled to absorb the liquid (not shown). The atomizer 32 has a first end electrically coupled to the atomizer assembly body 28 and a second end electrically coupled to the electrical coupler 22. The electrical circuit is completed when the cartridge is engaged with the power supply portion, discussed hereinbefore. The atomizing chamber 38 is thusly sealed but for the entry of fresh air through air inlet port 26 and the exit of air and aerosol up chimney 36 and out aerosol outlet 5.

Reference is directed to FIGS. 11a, 11b, 11c, and 11d, which are a first end view, a first side section view, a second end view, and a second side section view drawing, respectively, of an atomizing assembly 28 according to an illustrative embodiment of the present invention. The assembly is based on a metal body 28 that has a electrical coupler 22 insulatively supported 24 therein. The electrical coupler 22 has an air inlet port formed therethrough. The electrical coupler has a pair of air recesses 27 machined on its face so that an air channel is created when the cartridge is engaged with the power supply portion of the electronic cigarette. In this manner, the air path is from the exterior, through the air inlet vents 16, through the air recesses 27, through the air inlet port 26 of the electrical coupler and u to the atomizer 32. The wick 37 is positioned through the central cavity of the atomizer 32 and extends through the pair of semicircular recesses 30 in the body 28. The wick is a fibrous bundle, which is formed from a temperature resistant material, and may be selected from amongst aramid, fluorocarbon, sulfide, melamine, polyimide, carbon, and glass fibers. Or, from other suitable materials known to those skilled in the art.

Figures 12A, 12B, 13A, 13B:
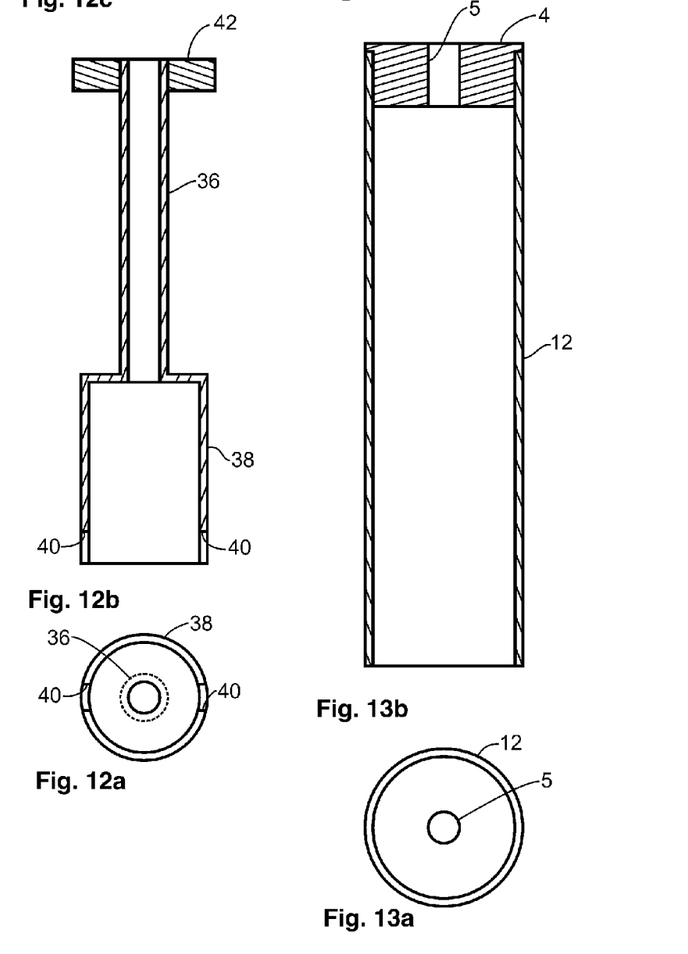
FIGS. 12a, 12b, and 12c are a first end view, a side section view, and a second end view drawing, respectively, of an atomizing chamber according to an illustrative embodiment of the present invention.
FIGS. 13a, 13b, and 13c are a first end view, a side section view, and a second end view drawing, respectively, of a mouthpiece housing according to an illustrative embodiment of the present invention.
Figure 12C:
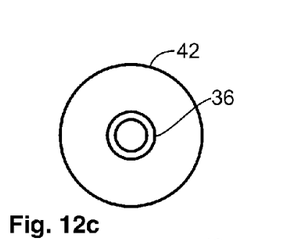

Reference is directed to FIGS. 12a, 12b, and 12c, which are a first end view, a side section view, and a second end view drawing, respectively, of an atomizing chamber 38 and chimney 6 according to an illustrative embodiment of the present invention. In the illustrative embodiment, the atomizing chamber 38 and chimney 36 are formed as a single unit. The atomizing chamber 38 and the chimney 36 are cylindrical in form. The resilient seal 42 is a donut shaped polymeric material that is pressed onto the upper end of the chimney 36. The atomizing chamber 38 includes a pair of opposing wick apertures 40 formed therein, which provide clearance for the wick (not shown) to pass into the atomizing chamber 38.

Figure 13C:
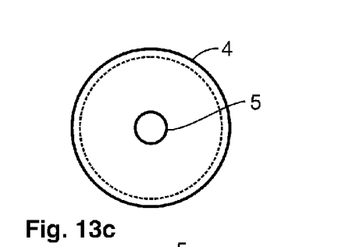

Reference is directed to FIGS. 13a, 13b, and 13c, which are a first end view, a side section view, and a second end view drawing, respectively, of a mouthpiece housing 12 according to an illustrative embodiment of the present invention. The housing 12 is a cylindrical plastic tube in the illustrative embodiment. The plastic is transparent or translucent to facilitate visual inspection of the liquid content. The tip end resilient insert 4, with the aerosol outlet port 5, closes the upper end of the cartridge housing 12.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. An electronic cigarette cartridge apparatus, comprising:
   an elongated housing having a mouthpiece with an aerosol outlet;
   an atomizer disposed within an atomizing chamber, and operable to selectively generate an aerosol of the liquid in response to electric current flowing therethrough;
   said atomizing chamber having an air inlet, an atomizer outlet coupled to said aerosol outlet, and a first wick aperture;
   a liquid reservoir disposed within said elongated housing and separated from said atomizing chamber, and
   a wick disposed within said atomizer and extending to an outer periphery of said atomizing chamber and configured to transfer the liquid by capillarity from said liquid reservoir, through said wick aperture, through said wick, and into to said atomizer.

2. The apparatus of claim 1, further comprising:
   an inlet vent formed on the exterior of said elongated housing and coupled to deliver air to said atomizing chamber air inlet.

3. The apparatus of claim 2, and wherein said inlet vent is coupled to said atomizing chamber air inlet by a conduit.

4. The apparatus of claim 3, and wherein said conduit sealably passes through said liquid reservoir.

5. The apparatus of claim 1, and wherein said atomizer outlet and said aerosol outlet are coupled by a chimney.

6. The apparatus of claim 5, and wherein said chimney sealably passes through said liquid reservoir.

7. The apparatus of claim 1, and wherein said atomizer is a resistive heating element.

8. The apparatus of claim 1, and wherein said atomizer has a tubular form defining an open central passage.

9. The apparatus of claim 8, and wherein said wick passes through said open central passage.

10. The apparatus of claim 1, and wherein said wick is fabricated as a bundle of heat resistant fibers.

11. The apparatus of claim 10, and wherein said bundle of heat resistant fibers is fiberglass.

12. The apparatus of claim 10, and wherein said bundle of heat resistant fibers is fabricated from a material selected from; aramid, fluorocarbon, sulfide, melamine, polyimide, carbon, and glass.

13. The apparatus of claim 1, and wherein said liquid reservoir is formed as a cavity between the interior of said elongated housing and said atomizing chamber.

14. The apparatus of claim 1, and wherein said liquid reservoir includes an external access opening, for enabling addition of liquid into said liquid reservoir.

15. The apparatus of claim 14, and wherein said external access opening is a removable mouthpiece.

* * * * *